(12) United States Patent
Jeong et al.

(10) Patent No.: US 12,049,564 B2
(45) Date of Patent: Jul. 30, 2024

(54) POSITIVELY CHARGED NANOPARTICLES, USE THEREOF, AND PREPARATION METHOD THEREOF

(71) Applicant: KOREA INSTITUTE OF SCIENCE AND TECHNOLOGY, Seoul (KR)

(72) Inventors: Youngdo Jeong, Seoul (KR); Kwan Hyi Lee, Seoul (KR); Hyojin Lee, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 285 days.

(21) Appl. No.: 16/855,547

(22) Filed: Apr. 22, 2020

(65) Prior Publication Data

US 2021/0130613 A1 May 6, 2021

(30) Foreign Application Priority Data

Oct. 30, 2019 (KR) .......................... 10-2019-0136903

(51) Int. Cl.
| | | |
|---|---|---|
| *C08L 79/04* | (2006.01) | |
| *A61K 9/51* | (2006.01) | |
| *C08G 73/06* | (2006.01) | |
| *C08K 3/105* | (2018.01) | |
| *B82Y 5/00* | (2011.01) | |
| *B82Y 30/00* | (2011.01) | |
| *B82Y 40/00* | (2011.01) | |

(52) U.S. Cl.
CPC ............ *C08L 79/04* (2013.01); *A61K 9/5146* (2013.01); *C08G 73/06* (2013.01); *B82Y 5/00* (2013.01); *B82Y 30/00* (2013.01); *B82Y 40/00* (2013.01); *C08K 3/105* (2018.01)

(58) Field of Classification Search
CPC ... A61K 47/6923; A61K 9/5146; C08L 79/04; C08L 79/06; C08G 73/06; B82Y 5/00
See application file for complete search history.

(56) References Cited

U.S. PATENT DOCUMENTS 9,073,972 B2    7/2015  Kim et al.
2006/0251725 A1*  11/2006  Kim ..................... C07D 487/22
                                                    514/393

FOREIGN PATENT DOCUMENTS

KR    10-2009-0109809 A    10/2009

OTHER PUBLICATIONS

Meethal et al., Langmuir 2018, 34, p. 693-699. (Year: 2018).*
Premkumar et al., Chem. Asian J., 2010, 5, p. 2468-2476. (Year: 2010).*
Ethylenediamine, Sids Initial Assessment Report For 13th SIAM (Bern, Switzerland Nov. 6-9, 2001, p. 1-166. (Year: 2001).*
Sinha et al., J. Mater. Chem. B, 2018, 6, p. 7329. (Year: 2018).*
Corma et al., "Gold Nanoparticles in Organic Capsules: A Supramolecular Assembly of Gold Nanoparticles and Cucurbituril," Chem. Eur. J. (2007), vol. 13, pp. 6359-6364.
Lu, X. and E. Masson, "Formulation and Stabilization of Silver Nanoparticles with Curcurbit[n]urils (n = 5-8) and Cucurbituril-Based Pseudorotaxanes in Aqueous Medium," Langmuir (2011), vol. 27, pp. 3051-3058.
Office Action issued Aug. 30, 2020, in Korean Patent Application No. 10-2019-0136903.
Jana et al., "Supramolecular protection-mediated one-pot synthesis of cationic gold nanoparticles," Journal of Industrial and Engineering Chemistry, Sep. 18, 2019, pp. 1-6.

* cited by examiner

*Primary Examiner* — Michael G. Hartley
*Assistant Examiner* — Leah H Schlientz
(74) *Attorney, Agent, or Firm* — Birch, Stewart, Kolasch & Birch, LLP

(57) ABSTRACT

Provided are positively charged nanoparticles and use thereof. According to the nanoparticles of an aspect, cucurbituril may limit electrostatic attraction between a guest for cucurbituril and a metal salt, thereby generating nanoparticles with a uniform size. Accordingly, the nanoparticles may have an effect of being capable of efficient intracellular gene delivery.

10 Claims, 16 Drawing Sheets

POSITIVELY CHARGED NANOPARTICLES, USE THEREOF, AND PREPARATION METHOD THEREOF

CROSS-REFERENCE TO RELATED APPLICATION

This application claims the benefit of Korean Patent Application No. 10-2019-0136903, filed on Oct. 30, 2019, in the Korean Intellectual Property Office, the disclosure of which is incorporated herein in its entirety by reference.

BACKGROUND

1. Field

The present disclosure relates to one-pot synthesis of positively charged nanoparticles, and use thereof.

2. Description of Related Art

Treatment of a disease by delivering a therapeutic gene to a desired organ in the body and allowing intracellular expression of a new protein is called gene therapy. Gene therapy may have excellent selectivity, as compared with general pharmacotherapy, and may improve a treatment rate and a treatment time of diseases which are difficult to treat by other therapies, and thus may be applied for a long period of time. Gene therapy is not for treating symptoms of a disease, but rather treats and eliminates the cause of a disease.

In order to effectively perform such gene therapy, it is necessary to develop gene delivery technology for delivering a therapeutic gene to a desired target cell to obtain high expression efficiency. Gene delivery carriers are required to have low toxicity or no toxicity, and to selectively and effectively deliver a gene to target cells. Such gene delivery carriers may be largely divided into viral and non-viral carriers. Viral gene delivery carriers composed of retroviruses (RV), adenoviruses (AV), and adeno-associated viruses (AAV) are excellent in terms of expression rate and sustainability, but their safety problems caused by immune responses have been pointed out. Non-viral gene delivery carriers mainly consist of cationic lipids or polymers, which form complexes by ionic bonds with anionic DNA to be delivered into cells. Non-viral carriers such as cationic liposomes, etc. are of interest because they have advantages such as biodegradability, low toxicity, non-immunogenicity, and ease of use, as compared with viral carriers. However, their biggest disadvantage is low gene transfer efficiency, as compared with viral carriers.

In 1999, an 18-year-old boy died while participating in gene therapy using an adenovirus at the University of Pennsylvania, and the US Food Safety Administration and the National Institutes of Health have discontinued all gene therapy clinical trials using adenoviruses. As a result of this incident, interest in safe gene delivery carriers has been gradually increasing, and studies on non-viral gene delivery carriers have recently received much attention. Positively charged gold nanoparticles have attracted much attention as a new platform for non-viral carriers with high efficiency. To synthesize positively charged gold nanoparticles, two or more stages of synthesis are needed. The reason why synthesis of positively charged gold nanoparticles through a single reaction is difficult is interaction between a positively charged ligand and a negatively charged gold atom, which do not form uniform nanoparticles, but form particles having an aggregated form and a non-uniform size. In existing methods, two or more stages are employed to synthesize positively charged nanoparticles with a uniform size. The methods are disadvantageous in that between the stages, a separation process is included, and mass production is difficult due to process complexity of two or more stages of synthesis, overuse of materials, and increased production costs due to the separation process, and applications are limited due to expensive materials.

SUMMARY

An aspect provides nanoparticles including a metal salt, cucurbituril, and a guest for cucurbituril.

Another aspect provides a method of preparing nanoparticles, the method including mixing a metal salt, cucurbituril, and a guest for cucurbituril, and reducing the mixture obtained from the mixing.

Additional aspects will be set forth in part in the description which follows and, in part, will be apparent from the description, or may be learned by practice of the presented embodiments of the disclosure.

An aspect provides nanoparticles including a metal salt, cucurbituril, and a guest for cucurbituril.

In one specific embodiment, the guest for cucurbituril may be a compound represented by the following Formula 1:

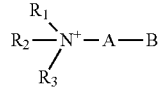

[Formula 1]

wherein, in Formula 1, $R_1$, $R_2$, and $R_3$ may be each independently any one selected from the group consisting of hydrogen, $C_1$-$C_{10}$ alkyl, $C_1$-$C_{10}$ alkenyl, alkynyl, and benzyl; A may be any one selected from the group consisting of substituted or unsubstituted $C_1$-$C_{40}$ alkyl, substituted or unsubstituted alkenyl, and substituted or unsubstituted alkynyl; and B may be any one selected from the group consisting of a hydroxyl group, thiol, thioether, sulfone, sulfoxide, amine, and a silane group.

Further, $R_1$, $R_2$, and $R_3$ may be each independently any one selected from the group consisting of hydrogen, $C_1$-$C_5$ alkyl, $C_1$-$C_5$ alkenyl, $C_1$-$C_5$ alkynyl, and benzyl; A may be any one selected from the group consisting of substituted or unsubstituted $C_1$-$C_{15}$ alkyl, substituted or unsubstituted $C_1$-$C_{15}$ alkenyl, and substituted or unsubstituted $C_1$-$C_{15}$ alkynyl; and B may be any one selected from the group consisting of a hydroxyl group and thiol.

B may be any functional group, as long as it is able to bind to a metal, but is not limited to those described above. In one embodiment of the present disclosure, $R_1$, $R_2$, and $R_3$ may be each independently methyl, A may be $C_{11}$ alkyl, and B may be thiol.

The term "substituted", for example, substituted alkyl group means that the alkyl group may be substituted with atoms other than the atoms (i.e., carbon and hydrogen atoms) commonly present in such a group. For example, the substituted alkyl group may include a halogen atom or a thiol group. The unsubstituted alkyl group includes only carbon and hydrogen atoms.

Unless otherwise specified, the substituted alkyl group, the substituted alkenyl group, and the substituted alkynyl group may be substituted with one or more substituents selected from the group consisting of a methyl group, an ethyl group, an n-propyl group, an isopropyl group, an n-butyl group, a 1-isobutyl group, a 2-isobutyl group, a t-butyl group, ester, amide, ether, thioether, ketone, aldehyde, sulfoxide, sulfone, sulfonate ester, sulfone amide, —Cl, —Br, —I, —OH, —SH, —CN, and —$NO_2$.

The cucurbituril is well known to form a host-guest compound (an inclusion compound) by binding to a large number of substances, and is a macrocyclic molecular compound having a hydrophobic cavity and hydrophilic portals at both sides thereof. Therefore, hydrophobic interaction occurs in the cavity of cucurbituril, and hydrogen bonding, polar interaction, cation-polar interaction, etc. occurs at the upper and lower portals thereof at which n carbonyl groups are located, so that cucurbituril exhibits inclusion effects through extremely stable noncovalent binding with various kinds of compounds. Cucurbituril may include, as a guest molecule, ionic materials and large-polarity materials, e.g., gaseous compounds, various organic materials, such as, aliphatic compounds, aromatic compounds, etc., and various kinds of compounds, such as insecticides, herbicides, amino acids, nucleic acids, ionic compounds, metallic ions, organic metallic ions, etc. In particular, cucurbituril may include more strongly and more selectively amine group-introduced molecules than other molecules. This interaction is called "host-guest interaction". Such a cucurbituril may include, for example, a glycoluril molecule as a unit, and may be synthesized by polymerizing the same equivalents of glycoluril and formaldehyde under a strong acid.

In a specific embodiment, the cucurbituril may be cucurbit[n]uril, cucurbit[6]uril, cucurbit[7]uril, cucurbit[8]uril, or cucurbit[10]uril.

The terms cucurbituril and cucurbit[n]uril may be used interchangeably. The cucurbituril used in one embodiment of the present disclosure is cucurbit[7]uril.

The guest for cucurbituril is a compound capable of forming a host-guest complex with cucurbituril. The guest may be ionic, for example, cationic or anionic, and there may be a suitable counter ion.

The guest for cucurbituril of the present disclosure noncovalently binds via cucurbituril-based host-guest interaction. In the present disclosure, the presence of the host-guest complex is confirmed by analysis of NMR spectrum of the product. The presence of the host-guest complex may be confirmed by another method such as UV-vis spectroscopy, as known to those skilled in the art.

When one guest is included in the cavity of cucurbituril, an association constant ($K_a$) thereof is at least $10^3$ $M^{-1}$, at least $10^4$ $M^{-1}$, at least $10^5$ $M^{-1}$, at least $10^6$ $M^{-1}$, at least $10^7$ $M^{-1}$, at least $10^8$ $M^{-1}$, at least $10^9 M^{-1}$, at least $10^{10}$ $M^{-1}$, at least $10^{11}$ $M^{-1}$, or at least $10^{12}$ $M^{-1}$. In one embodiment of the present disclosure, the guest is a compound capable of forming a complex having an association constant in the range of $10^5$ $M^{-1}$ to $10^7$ $M^{-1}$ with cucurbituril.

In one specific embodiment, the metal salt is $NaAuCl_4 \cdot 2H_2O$, $HAuCl_4 \cdot 3H_2O$, $NaAuBr_4 \cdot xH_2O$, $KAuCl_4$, $NaAuCl_4$, $HAuCl_4$, $NaAuBr_4$, $KAuBr_4$, $HAuBr_4$, $AuCl_3$, $AuBr_3$, or $AuCl_3$, wherein x is 1 to 5, but is not limited thereto. In one embodiment of the present disclosure, the metal salt is $HAuCl_4 \cdot 3H_2O$.

In one specific embodiment, the nanoparticles may be synthesized by reduction in an aqueous medium. The reduction may be performed by a reducing agent, such as $NaBH_4$, etc.

In a specific embodiment, at least part of the guest for cucurbituril may exist as a complex with cucurbituril. The part of the guest for cucurbituril may be an ionic moiety. In one embodiment of the present disclosure, the part of the guest for cucurbituril forming the complex with cucurbituril may be a cationic moiety.

In one specific embodiment, the nanoparticles may be positively charged. The nanoparticles may be positively charged by electrostatic attraction with a positively charged compound. Further, since the nanoparticles are positively charged, it may intracellularly deliver a negatively charged material.

In one specific embodiment, the cucurbituril may reduce electrostatic attraction between the guest for cucurbituril and the metal salt. The cucurbituril interacts with the positively charged moiety of the guest for cucurbituril to reduce strength of the positive charge, thereby reducing electrostatic attraction between the metal salt and the guest for cucurbituril.

In one specific embodiment, sizes of the nanoparticles may be uniform. The sizes of the nanoparticles may be not polydisperse but uniform by using cucurbituril.

In one specific embodiment, the nanoparticles may be for gene delivery. The nanoparticles may intracellularly deliver a negatively charged gene such as DNA or RNA.

Another aspect provides a method of preparing the nanoparticles, the method including mixing the metal salt, the cucurbituril, and the guest for cucurbituril, and reducing the mixture obtained from the mixing.

In one specific embodiment, the preparation method may be performed in one pot.

The term "one-pot" means that several stages are continuously carried out in one reactor except for intermediate processes such as intermediate purification, recovery, and pulverization.

In one specific embodiment, the preparation method may be carried out in an aqueous medium.

The aqueous medium which is a medium containing water may be water or deionized water, or may be a mixture. For example, the aqueous medium may further include optionally one or more water-soluble organic solvents, such as lower alcohols such as ethanol, lower glycols such as ethylene glycol, and lower ketones such as methyl ethyl ketone.

Of the terms or elements mentioned in the method of preparing nanoparticles, those mentioned in the description of the claimed nanoparticles are understood as being mentioned in the description of the claimed nanoparticles in advance.

DETAILED DESCRIPTION

Figure 1A:
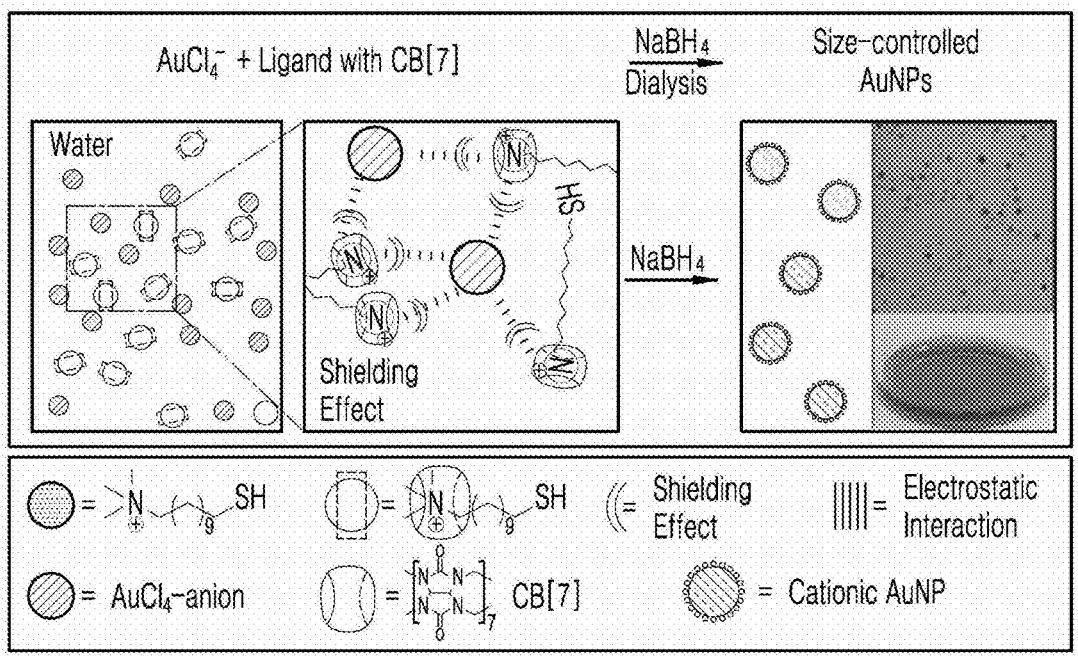
FIG. 1 is an illustration of a synthetic process of cationic gold nanoparticles (AuNPs) in the presence or absence of cucurbituril, and the size of AuNPs in each case.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Preparation Example 1. Experimental Materials and Experimental Preparation 1-1. Experimental Materials Celltiter 96® aqueous one solution cell proliferation assay (MTS) kit was purchased from Promega Korea, Ltd. 10× Phosphate buffered saline (PBS), dulbecco's modified eagle medium (DMEM), fetal bovine serum (FBS), and penicillin and streptomycin (PIS, 100×) were purchased from WEL-GENE, Korea.

Tetrachloroauric acid (III) trihydrate (HAuCl$_4$·3H$_2$O), azobisisobutyronitrile (AIBN), thioacetic acid, trimethyl amine (NMe$_3$), sodium methoxide (NaOMe), and cucurbituril (CB) hydrate were purchased from Sigma Aldrich. Sodium borohydride (NaBH$_4$) was purchased from Acros Organics. 10-Undecenyl bromide was purchased from TCI, Japan. All chemicals were used without additional purification.

1-2. DLS Measurement

Aqueous solutions of AuNP (w/CB) and AuNP (w/o CB) were separately prepared, and a zeta size and a zeta potential were measured using Malvern Zetasizer ZS series (UK). Mean data were obtained from three individual measurements.

1-3. UV Measurement

Aqueous solutions of AuNP (w/CB) and AuNP (w/o CB) were separately prepared, and UV spectra were recorded using a JASCO V-670 spectrometer.

1-4. Transmission Electron Microscopy (TEM) Study

Each one drop of aqueous solutions of AuNP (w/CB) and AuNP (w/o CB) was put on a 300-mesh formvar/carbon-coated copper grid, and evaporated under ambient condition for 6 hours or longer. Samples were observed under TEM (JEM-1400) operated at 120 kV. Images were obtained using a BioTEM system. Data were analyzed using a Gatan Digital Micrograph program.

1-5. Loading Capacity Test and Polyanionic Heparin Competitive Assay

For loading capacity test and polyanionic heparin competitive assay of siRNA/AuNP complex, polyacrylamide gel electrophoresis (PAGE) analysis was performed. 25 pmol of siRNA was incubated with various concentrations (0 μg~3 μg) of AuNPs in 20 μL of 1×PBS. After 1 hr-incubation, a gel was stained with a SYBR gold staining reagent. For polyanionic heparin competitive assay, heparin (0 μg~50 μg) was added to the siRNA/AuNP mixture to induce release of siRNA from AuNP, before gel electrophoresis.

1-6. RNase Protective Assay

To evaluate siRNA protection from RNase-mediated degradation in the presence of AuNP, PAGE analysis was performed. RNase (25 μg) was first incubated with siRNA or siRNA/AuNP complex in 20 μL of PBS for 1 hr, followed by gel electrophoresis and SYBR gold staining.

1-7. Cell Culture

Human cervical cancer cell line was cultured in DMEM containing 4.5 g/L of D-glucose, 10% FBS, 1% penicillin and streptomycin at 5% CO$_2$ and 37° C.

1-8. Cell Viability Assay

To assay cell viability of AuNP for biological application, GFP-HeLa cells (1×10$^4$ cells/well) were prepared triplicate in a 96-well plate for 24 hr, and then incubated with various concentrations of AuNP in a complete medium. After 12-hr incubation, cells were washed with 1×PBS, and then an MTS cell proliferation assay solution, together with a complete medium, was added thereto for 2 hr, and absorbance at 490 nm was measured using a microplate reader (TECAN, Infinite F200 Pro).

1-9. Flow Cytometry

GFP-HeLa cells (3×10$^4$ cells/well, 24-well plate) were treated with siRNA/AuNP complex in a serum-free medium for 12 hr (final volume; 500 μL, [siRNA]=50 nM). Subsequently, the cell culture medium was replaced by a serum-containing fresh medium, followed by incubation for 12 hr. The cells were washed with 1×PBS, and then treated with trypsin-EDTA for 3 min to collect cells. Then, 10% FBS was added to the collected cells, followed by centrifugation at 1,200 rpm for 3 min. Cells were finally washed with 1×PBS, and cell fluorescence was measured using a flow cytometer, FACS Canto (Becton Dickinson, USA)

1-10. Synthesis of HS-C11-TMA

Synthesis of 11-thioacetylundecyl bromide: 10-undecenyl bromide (1 g, 4.2 mmol) was dissolved in methanol, and then thioacetic acid (0.591 mL, 8.4 mmol) and AIBN (3.44 g, 21 mmol) were added thereto. The reaction mixture was refluxed at 70° C. for 15 hr. After completion of the reaction, 11-thioacetylundecyl bromide was purified by a silica gel column chromatography using an eluent with a ratio of hexane:ethyl acetate of 9:1.

Synthesis of N,N,N-trimethyl (11-mercaptoundecyl)-ammonium: 11-thioacetylundecyl bromide (1 g, 3.2 mmol) was added to $NMe_3$ (0.57 g, 9.6 mmol) in methanol, followed by stirring at room temperature for 2 days. A desired compound was precipitated in hexane, and precipitates were washed with hexane several times, followed by purification.

Synthesis of 11-N,N,N-trimethyl amino undecylthiol (HS-C11-TMA): N,N,N-trimethyl (11-mercaptoundecyl)-ammonium (0.2 g, 0.7 mmol) was dissolved in 3 mL of methanol. 1 mL of 0.1 M sodium methoxide (NaOMe) in methanol was added, followed by stirring at room temperature for 30 min. A desired product (HS-C11-TMA) was precipitated in ether. Precipitates were washed with ether, and dried to obtain a final product.

Example 1. Preparation of Cationic AuNPs with Tunable Size

Figure 1B:
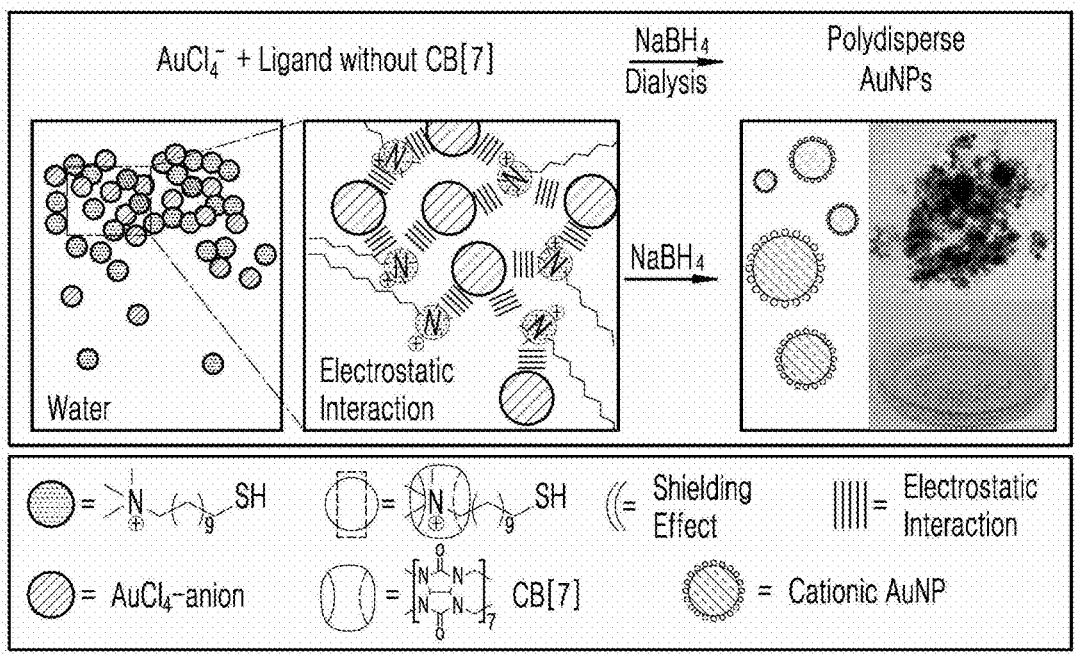

Cationic AuNPs with tunable size were prepared in an aqueous medium by one-pot synthesis based on host-guest chemistry. N,N,N-trimethyl-11-sulfanyl-1-undecanaminium chloride (HS-C11-TMA) (FIG. 2) was used as a cationic ligand. Cucurbituril was selected as a complementary host molecule due to its moderate water solubility, high binding affinity with cationic moieties, and compatibility in physiological environments. A complex of HS-C11-TMAs and CB was immediately produced due to modest binding affinity (Ka: ~3×10$^5$ M$^{-1}$) by mixing a molar ratio of 1:1 in water. As a host molecule, cucurbituril (CB) minimizes the electrostatic attraction between $AuCl_4^-$ anions and the positively charged ligand by threading guest alkylammonium cations. This shielding effect of CB on the ligands allows the mixture to be well dispersed, inhibiting ionic Au-ligand aggregation in an aqueous solution (FIG. 1). The host-guest complexation was confirmed by $^1H$ NMR spectroscopy analysis, in which the resonance signals attributed to the methylene groups (red circles and red stars) of the complex HS-C11-TMA@CB were shifted upfield relative to those of HSC11-TMA (FIG. 3). Then, direct reduction by adding $NaBH_4$ produces cationic AuNPs with no diverse size and with narrow size distributions (FIG. 1). The size of the AuNPs may be tuned by controlling a ratio between $AuCl_4^-$ and the CB-threaded ligands.

FIG. 1 is an illustration of a synthetic process of cationic gold nanoparticles (AuNPs) in the presence or absence of cucurbituril, and the size of AuNPs in each case.

Figure 2:
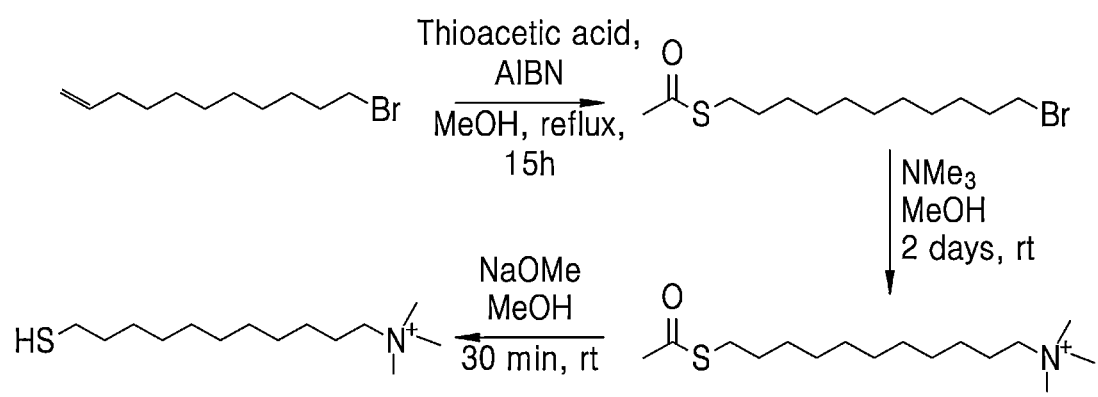
FIG. 2 is an illustration of a synthetic process of 11-N, N,N-trimethyl amino undecylthiol (HS-C11-TMA) which is a guest compound for cucurbituril used in one embodiment of the present disclosure.
Figure 3A:
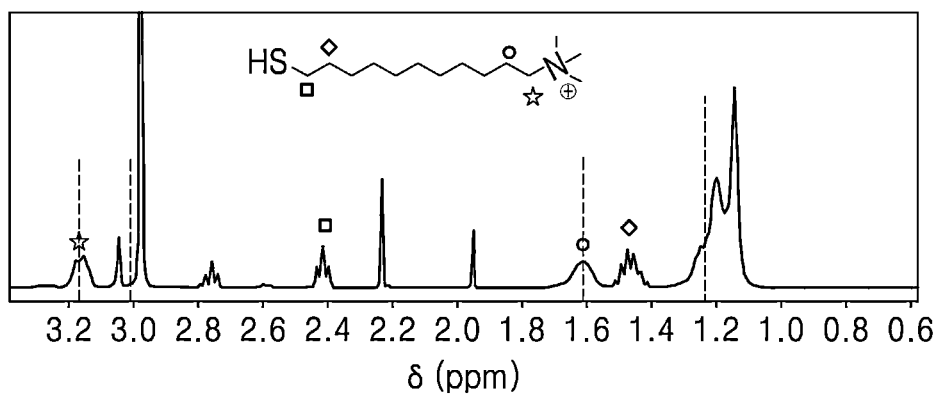
FIG. 3 is a graph showing $^1$H NMR signals of HS-C11-TMA in the presence or absence of cucurbituril.
Figure 3B:
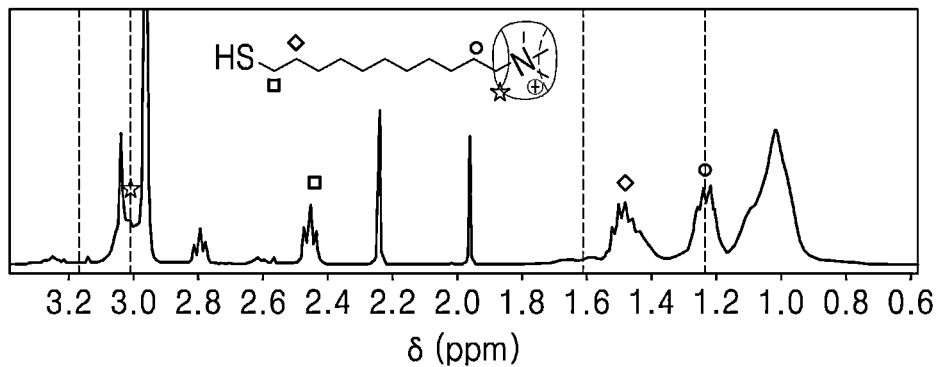

FIG. 2 is an illustration of a synthetic process of 11-N, N,N-trimethyl amino undecylthiol (HS-C11-TMA) which is the guest compound for cucurbituril used in one embodiment of the present disclosure.

FIG. 3 is a graph showing $^1H$ NMR signals of HS-C11-TMA in the presence or absence of cucurbituril.

Figure 4A:
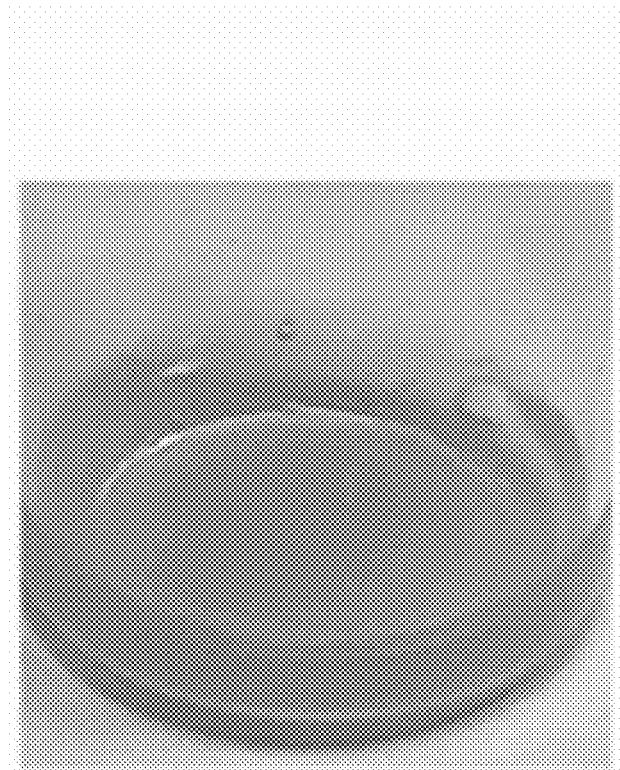
FIG. 4A is an image showing a mixture of $AuCl_4$— with HS-C11-TMA@CB in which cucurbituril bound to HS-C11-TMA.
Figure 4B:
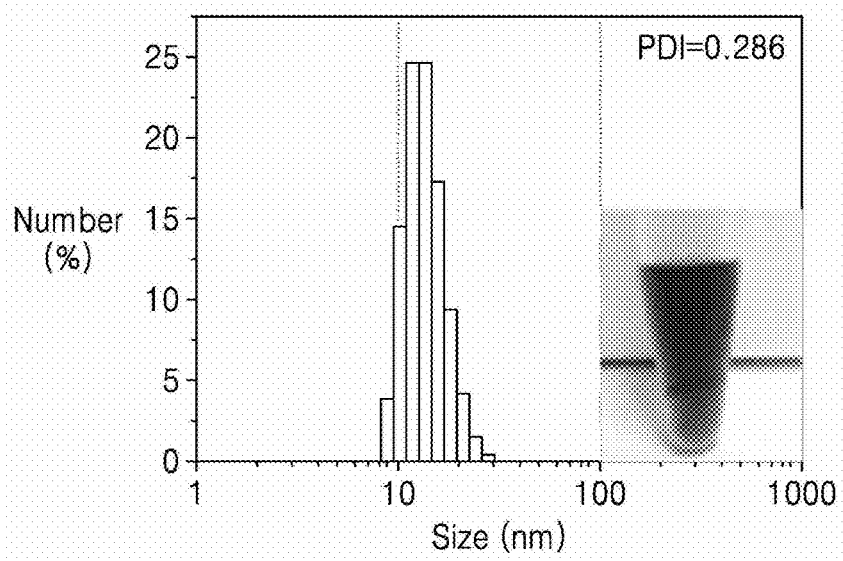
FIG. 4B is a graph showing DLS result of analyzing a size distribution of AuNPs formed by mixing HS-C11-TMA@CB with $AuCl_4$—, and an image showing precipitation.
Figure 4C:
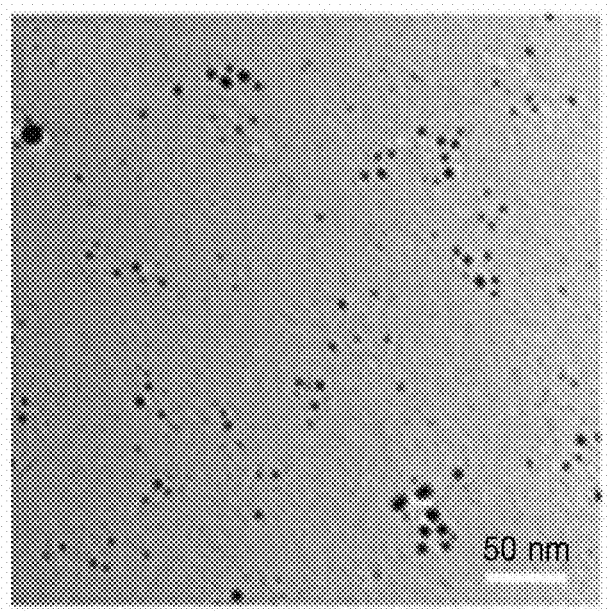
FIG. 4C is a TEM image of AuNPs formed by mixing HS-C11-TMA@CB with $AuCl_4$—.
Figure 4D:
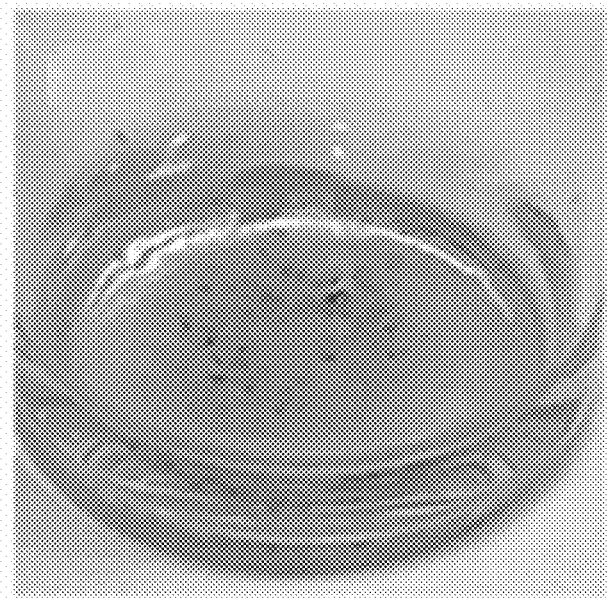
FIG. 4D is an image of a mixture of $AuCl_4$— with HS-C11-TMA without cucurbituril.

Experimental Example 1. Analysis of Shielding Effect of Cucurbituril (CB) on Electrostatic Attraction The interaction between HS-C11-TMAs and $AuCl_4^-$ anions in the presence and absence of CB was analyzed. As a result, in the absence of CB, HS-C11-TMAs produced insoluble precipitates in an aqueous solution due to the electrostatic attraction between $AuCl_4^-$ anions and the cationic moiety of the ligands, upon mixing with $AuCl_4^-$ (FIG. 4D). Meanwhile, in the mixture of $AuCl_4^-$ and HS-C11-TMA@CB, precipitates were hardly formed (FIG. 4A). This result suggests that CB threaded the quaternary ammonium group of the ligand, thereby preventing the formation of precipitates, which demonstrates the shielding effect of CB toward the electrostatic attraction.

Figure 4E:
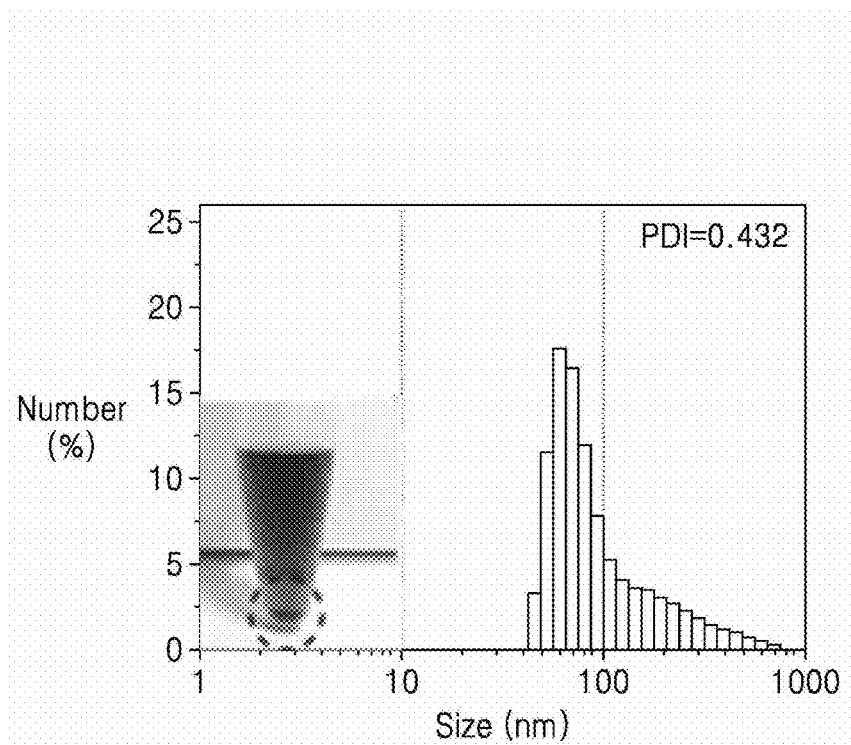
FIG. 4E is a graph showing DLS result of analyzing a size distribution of AuNPs formed by mixing AuCl$_4$— with HS-C11-TMA without cucurbituril, and an image showing precipitation.
Figure 4F:
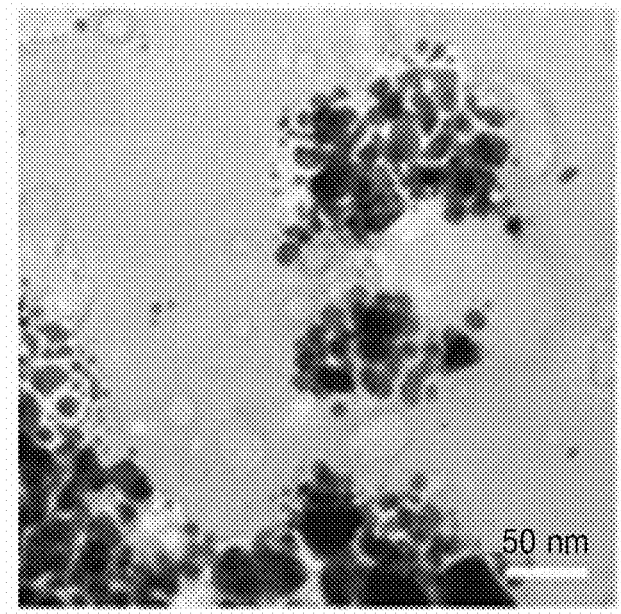
FIG. 4F is a TEM image of AuNPs formed by mixing AuCl$_4$— with HS-C11-TMA without cucurbituril.

To further investigate the shielding effect of CB on the synthesis of AuNP, a solution of $NaBH_4$ was directly added to the mixture of $AuCl_4^-$ and HS-C11-TMA in the presence or absence of CB. Transmission electron microscopy (TEM) and dynamic light scattering (DLS) analyses confirmed that polydisperse AuNPs were obtained in the absence of CB. In this case, a gold core had a diverse size distribution ranging from 4 nm to 100 nm, and a hydrodynamic diameter of the AuNPs ranged from 40 nm to 800 nm (FIGS. 4E and 4F). Due to the formation of larger AuNPs, a precipitate of AuNPs was observed after centrifugation of the mixture at 10000 rpm for 20 min (FIG. 4E). In contrast, cationic AuNPs with narrow size distributions were obtained in the presence of CB. In this case, the average size of the gold core was 5.5±1.7 nm, and the hydrodynamic diameter of AuNPs was 13.75±3.36 nm (FIGS. 4B and 4C).

Figure 5:
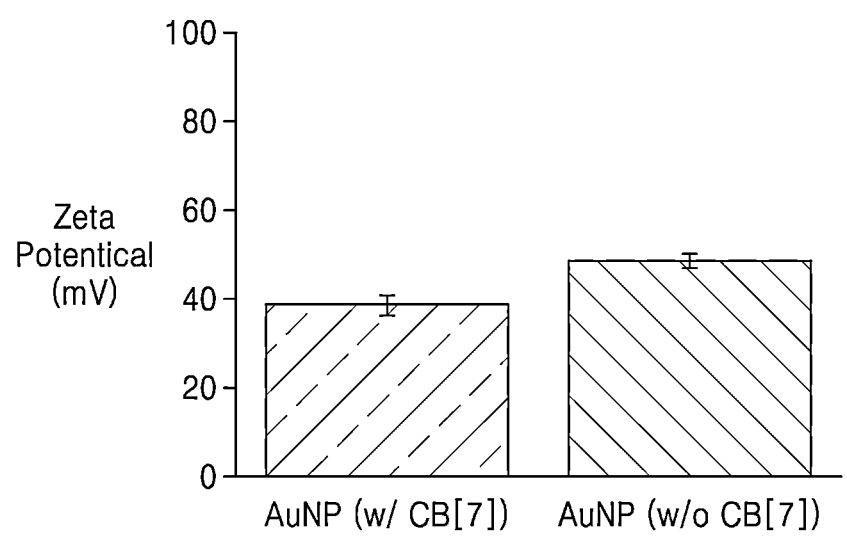
FIG. 5 is a graph showing result of measuring a zeta potential of AuNP in the presence or absence of cucurbituril.

Further, as a result of zeta potential measurement, a zeta potential of AuNPs synthesized with HS-C11-TMA@CB was +38.6±2.3 mV, and a zeta potential of AuNPs synthesized with HS-C11-TMA was +48.5±1.4 mV (FIG. 5).

These results indicate that CB prevented the cationic moieties of the ligands from electrostatically interacting with the $AuCl_4^-$ anions, conferring a shielding effect on the ligands for the synthesis of narrow-dispersed cationic AuNPs.

FIG. 4A is an image showing a mixture of $AuCl_4$— with HS-C11-TMA@CB in which cucurbituril bound to HS-C11-TMA; FIG. 4B is a graph showing DLS result of analyzing a size distribution of AuNPs formed by mixing HS-C11-TMA@CB with $AuCl_4$—, and an image showing precipitation; FIG. 4C is a TEM image of AuNPs formed by mixing HS-C11-TMA@CB with $AuCl_4$—; FIG. 4D is an image of a mixture of $AuCl_4$— with HS-C11-TMA without cucurbituril; FIG. 4E is a graph showing DLS result of analyzing a size distribution of AuNPs formed by mixing $AuCl_4$— with HS-C11-TMA without cucurbituril, and an image showing precipitation; and FIG. 4F is a TEM image of AuNPs formed by mixing $AuCl_4$— with HS-C11-TMA without cucurbituril.

FIG. 5 is a graph showing result of measuring a zeta potential of AuNP in the presence or absence of cucurbituril.

Experimental Example 2. Synthesis of AuNPs with Diverse Sizes

Figure 6:
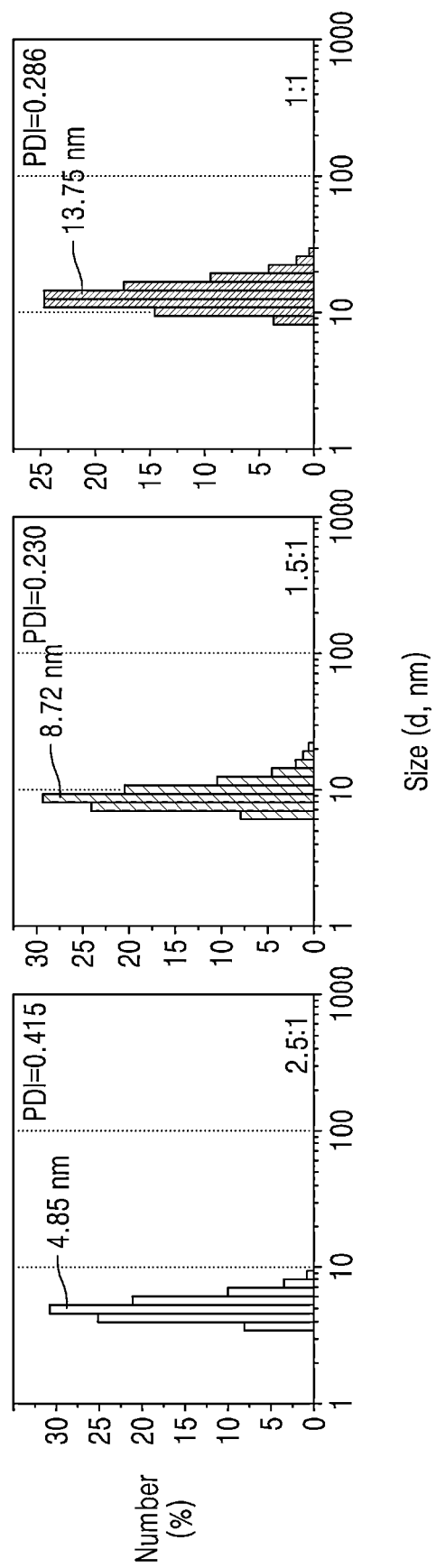
FIG. 6 is a graph showing DLS result of analyzing AuNPs prepared from AuCl$_4$— and HS-C10-TMA@CB at a molar ratio of 2.5:1, 1.5:1, and 1:1.
Figure 7:
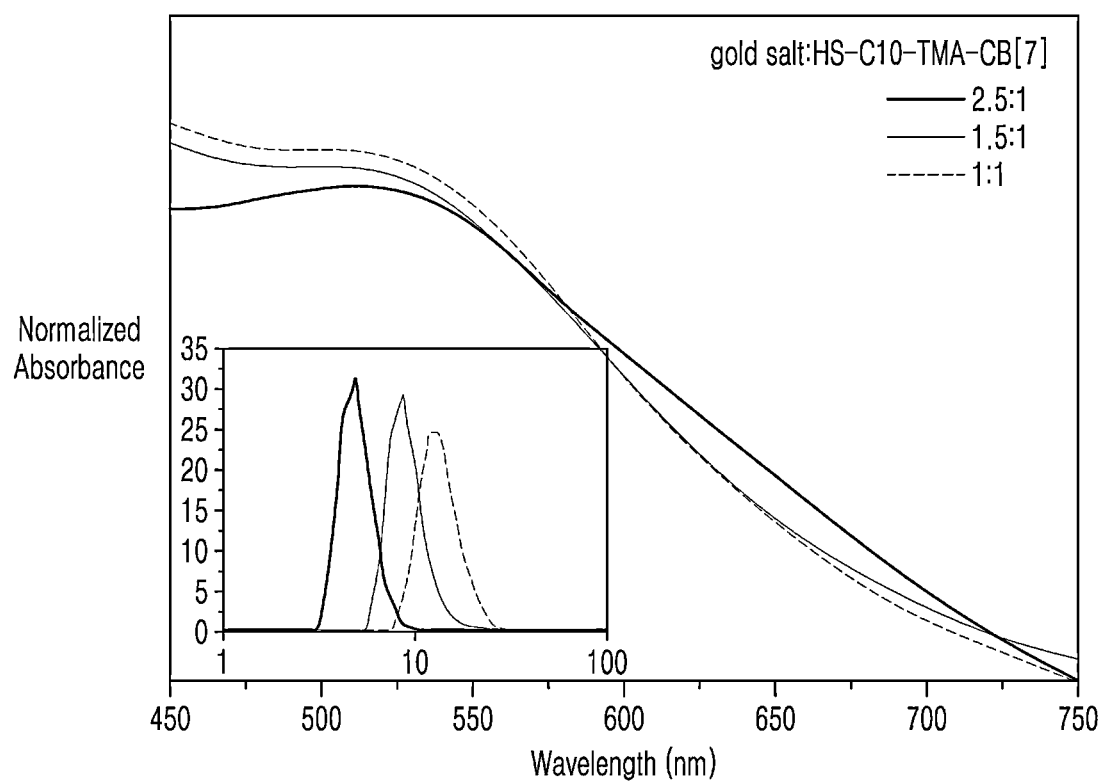
FIG. 7 is a graph showing UV-vis absorption spectroscopy result of analyzing sizes of AuNPs prepared from AuCl$_4$— and HS-C10-TMA@CB at a molar ratio of 2.5:1, 1.5:1, and 1:1.

The size of AuNPs obtained in Example 2 may be tuned by controlling a molar ratio of $AuCl_4^-$ and the CB-threaded ligand. Thus, the sizes of AuNPs prepared by controlling the molar ratio of $AuCl_4^-$ and the HS-C10-TMA@CB at 2.5:1, 1.5:1 and 1:1 were analyzed by using DLS and UV-vis absorption spectroscopy. As a result of DLS measurements, the size of the cationic AuNPs synthesized at a ratio of 2.5:1, 1.5:1 and 1:1 exhibited 6.7□1.9 nm, 9.5 □2.8 nm, and 13.7□3.4 nm, respectively, with narrow size distributions (FIGS. 6 and 7). Meanwhile, the UV-vis spectra showed the resonance wavelength of the surface plasmon on the AuNPs (FIG. 7). These results indicate that various cationic AuNPs may be synthesized by controlling the molar ratio between AuCl$_4^-$ and the ligand through the shielding effect of CB.

FIG. 6 is a graph showing DLS result of analyzing AuNPs prepared from AuCl$_4$— and HS-C10-TMA@CB at a molar ratio of 2.5:1, 1.5:1, and 1:1.

FIG. 7 is a graph showing UV-vis absorption spectroscopy result of analyzing sizes of AuNPs prepared from AuCl$_4$— and HS-C10-TMA@CB at a molar ratio of 2.5:1, 1.5:1, and 1:1.

Experimental Example 3. Cytotoxicity Analysis of AuNPs

Figure 8:
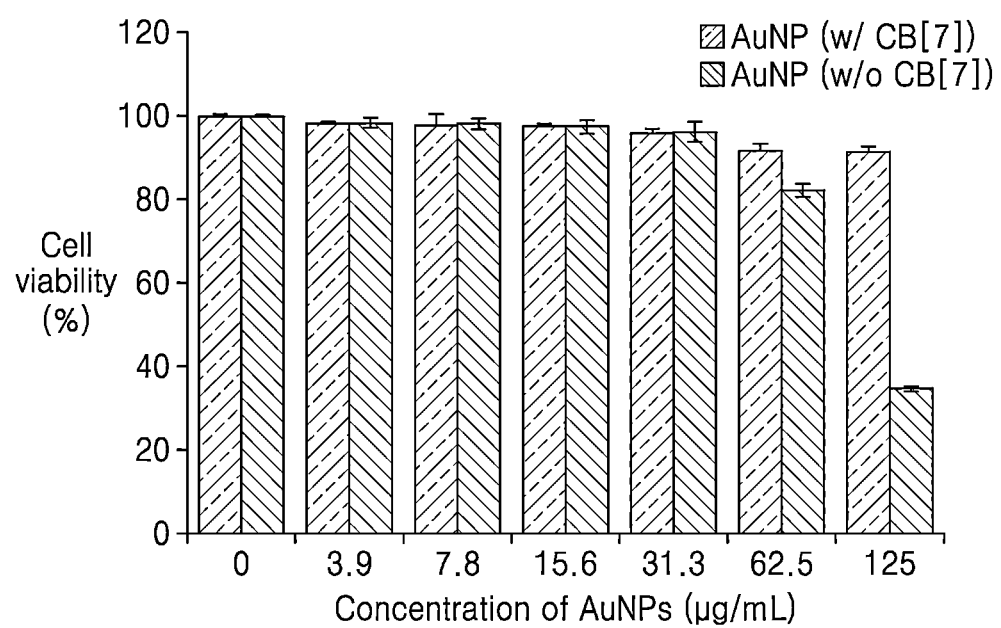
FIG. 8 is a graph showing cytotoxicity of AuNP in the presence or absence of cucurbituril.

To examine cytotoxicity of AuNPs, cell viability of HeLa cells was evaluated using an MTS cell proliferation assay kit, after treatment with various concentrations of AuNPs for 24 hours (FIG. 8). As a result, 80% or more of the cells survived at a concentration of 0 µg/mL to 62.5 µg/mL of AuNPs, irrespective of the presence of CB. This result indicates that cationic AuNPs are biocompatible.

FIG. 8 is a graph showing cytotoxicity of AuNP in the presence or absence of cucurbituril.

Experimental Example 4. Analysis of Gene Delivery Efficacy of AuNPs

Figure 9:
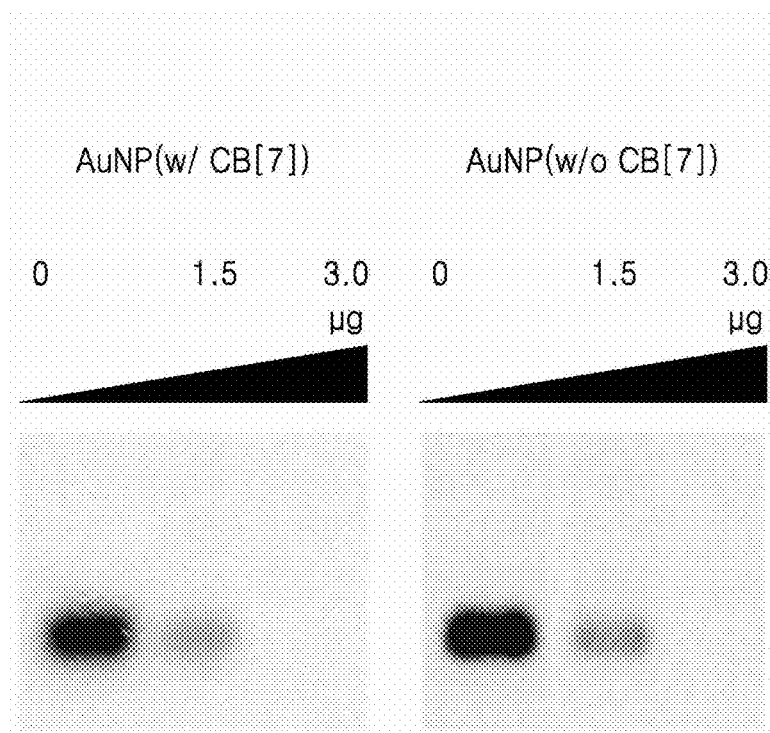
FIG. 9 shows PAGE results of siRNA/AuNP complexes obtained by mixing siRNA and AuNP in the presence or absence of cucurbituril.

To demonstrate biomedical function of the synthesized cationic AuNPs, intracellular-delivery experiment was performed. To allow facile monitoring of the gene delivery efficacy, siRNA that knockdowns green fluorescence proteins (GFP) was used as a biomacromolecule for delivery. First, the formation of the siRNA/AuNP complex and the siRNA loading capacity of the AuNPs synthesized in the absence or presence of CB were evaluated by polyacrylamide gel electrophoresis (PAGE) analysis. Upon mixing siRNA and AuNPs in a phosphate buffered solution, siRNA/AuNPs complexes were formed via electrostatic interaction between the siRNA and the cationic AuNPs. The siRNA/AuNPs complexes produced by mixing 25 pmol of siRNA and different amounts of AuNPs prepared with and without CB (0 µg, 1.5 µg, and 3 µg) were loaded into the gel. As a result of electrophoresis, the band intensity of the siRNA was found to decrease with increasing the amount of cationic AuNPs, confirming the formation of the siRNA/AuNP complex. The PAGE results indicated that 25 pmol of siRNA is loaded with 2 µg of cationic AuNPs (FIG. 9).

Figure 10:
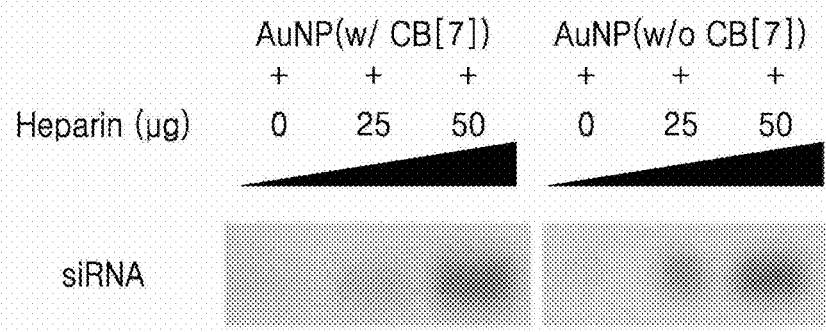
FIG. 10 shows PAGE results of analyzing amounts of siRNA released from siRNA/AuNP complexes according to heparin concentrations, the siRNA/AuNP complexes obtained by mixing siRNA and AuNP in the presence or absence of cucurbituril.
Figure 11:
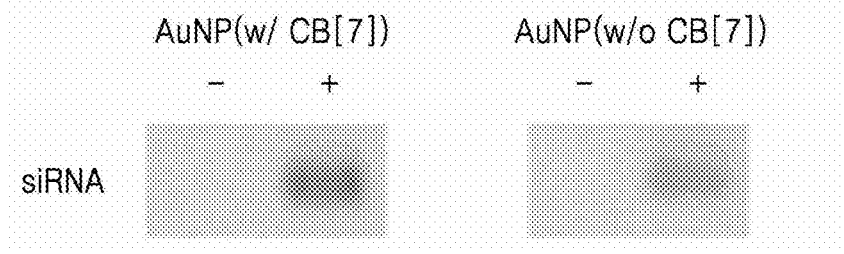
FIG. 11 shows PAGE results of analyzing amounts of siRNA upon treating siRNA/AuNP complexes with RNase and heparin, the siRNA/AuNP complexes obtained by mixing siRNA and AuNP in the presence or absence of cucurbituril.

Further, a polyanionic heparin competitive assay and a ribonuclease (RNase) protective assay were carried out to confirm the conditional release of siRNA from AuNPs and chemical stability of the complexed siRNA. As a result, as shown in FIG. 10, the band intensity of siRNA increased with increasing the amount of heparin, facilitating the release of siRNA from AuNPs. The PAGE analysis performed after stepwise incubation of RNase and heparin with the siRNA/AuNPs complexes showed their protective capability toward RNase-mediated degradation, due to condensation of siRNA with the cationic AuNPs (FIG. 11). These results indicate that the quaternary ammonium-functionalized AuNPs may be used as gene delivery carriers.

Figure 12:
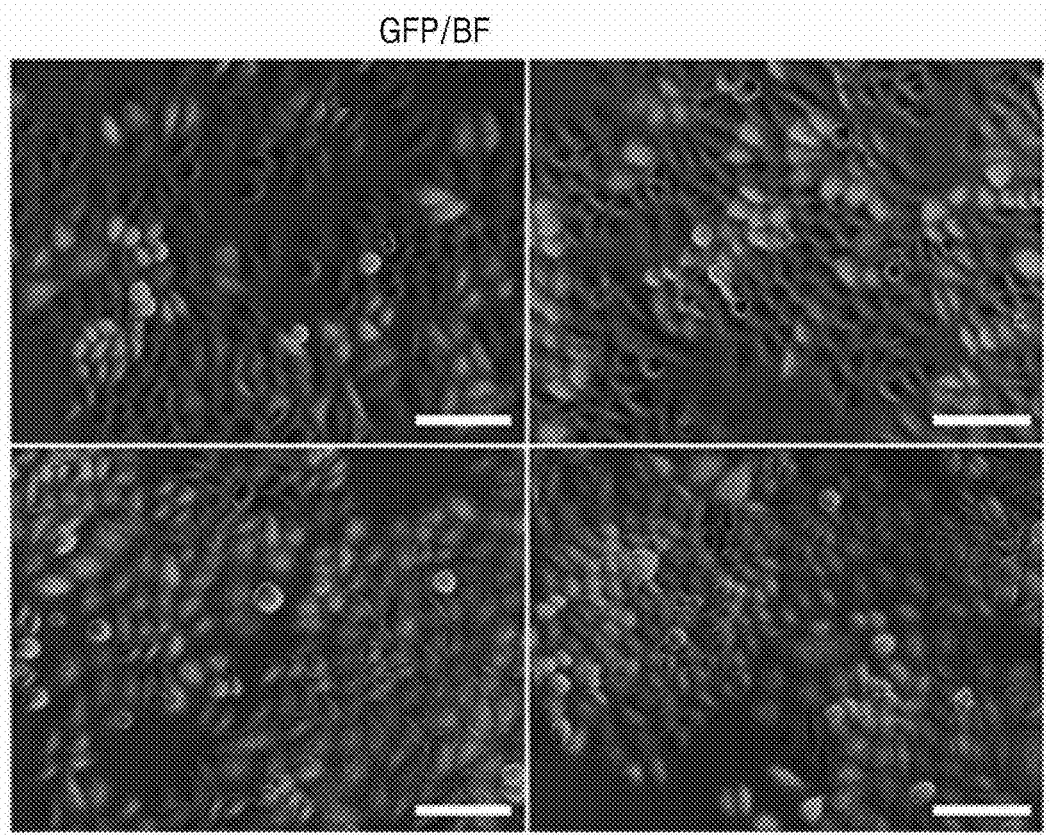
FIG. 12 shows fluorescence microscopy images of, clockwise from top left, GFP-HeLa cells cultured with siRNA/AuNP complexes in the presence of cucurbituril, GFP-HeLa cells cultured with siRNA/AuNP complexes in the absence of cucurbituril, GFP-HeLa cells cultured with only siRNA, and only GFP-HeLa cells cultured.

Next, down-regulation of GFP expression induced by the siRNA/AuNPs complexes in GFP-expressing HeLa (GFP-HeLa) cells was quantitatively evaluated. The cells were incubated with siRNA/AuNPs complex composed of 50 nM siRNA and 4 µg/mL AuNPs for 12 hr, followed by removing the medium and further incubating with a fresh serum-containing medium for 12 hr. The relative gene expression level of GFP was evaluated by monitoring the fluorescent intensity of the cells via microscope imaging and flow cytometry. As a result, as shown in FIG. 12, the green fluorescent intensities decreased in the siRNA/AuNPs-treated cells, as compared with those treated with AuNPs only. This result indicates a knockdown of the green fluorescent proteins via siRNA transfection.

Figure 13:
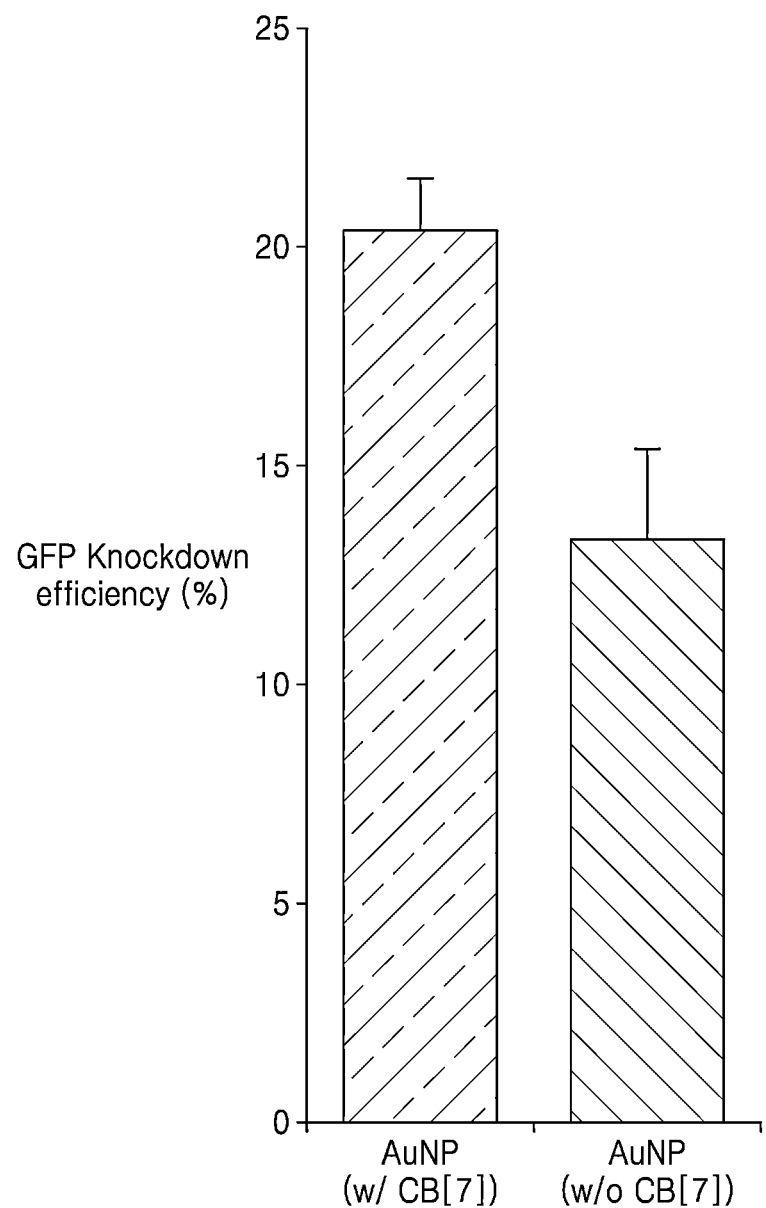
FIG. 13 is a graph showing flow cytometry results of analyzing gene knockdown efficacy of siRNA/AuNP complexes in the presence or absence of cucurbituril.

Further, the flow cytometric data representing cell population versus fluorescent intensity further confirmed that the gene silencing efficiency of the siRNA/AuNPs complexes in which AuNPs were prepared with CB exhibited higher knockdown efficacy of 20.4% than 13.3% of those containing AuNPs prepared in the absence of CB (FIG. 13). These results indicate that the cationic AuNPs with a narrow size distribution which were prepared with CB may perform better gene transfection efficacy than cationic AuNPs with a wide size distribution.

FIG. 9 shows PAGE results of siRNA/AuNP complexes obtained by mixing siRNA and AuNP in the presence or absence of cucurbituril.

FIG. 10 shows PAGE results of analyzing amounts of siRNA released from siRNA/AuNP complexes according to heparin concentrations, the siRNA/AuNP complexes obtained by mixing siRNA and AuNP in the presence or absence of cucurbituril.

FIG. 11 shows PAGE results of analyzing amounts of siRNA upon treating siRNA/AuNP complexes with RNase and heparin, the siRNA/AuNP complexes obtained by mixing siRNA and AuNP in the presence or absence of cucurbituril.

FIG. 12 shows fluorescence microscopy images of, clockwise from top left, GFP-HeLa cells cultured with siRNA/AuNP complexes in the presence of cucurbituril, GFP-HeLa cells cultured with siRNA/AuNP complexes in the absence of cucurbituril, GFP-HeLa cells cultured with only siRNA, and only GFP-HeLa cells cultured.

FIG. 13 is a graph showing flow cytometry results of analyzing gene knockdown efficacy of siRNA/AuNP complexes in the presence or absence of cucurbituril.

According to nanoparticles and a method of preparing the nanoparticles according to an aspect, cucurbituril may limit electrostatic attraction between a guest for cucurbituril and a metal salt, and thus nanoparticles with a uniform size may be formed by a single reaction. Accordingly, the nanoparticles may have an effect of being capable of efficient intracellular gene delivery It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the disclosure as defined by the following claims.

What is claimed is:

1. A method of preparing a gold nanoparticle, the method comprising:
   mixing a gold salt, cucurbituril, and guest for cucurbituril; and
   reducing the mixture obtained from the mixing thereby obtaining said gold nanoparticle;
   wherein the gold nanoparticle further comprises DNA or RNA;

wherein the gold salt is selected from the group consisting of $NaAuCl_4 \cdot 2H_2O$, $HAuCl_4 \cdot 3H_2O$, $NaAuBr_4 \cdot xH_2O$, $KAuCl_4$, $NaAuCl_4$, $HAuCl_4$, $NaAuBr_4$, $KAuBr_4$, $HAuBr_4$, $AuCl_3$, $AuBr_3$, and $AuCl_3$, wherein x is 1 to 5; and wherein the guest for cucurbituril forms a host-guest complex with the cucurbituril as the host; and wherein the guest for cucurbituril is N,N,N-trimethyl-11-sulfanyl-1-undecanaminium.

2. The method of claim 1, wherein the method is carried out in one pot.

3. The method of claim 1, wherein the method is carried out in an aqueous medium.

4. The method of claim 1, wherein the cucurbituril is cucurbit[5]uril, cucurbit[6]uril, cucurbit[7]uril, cucurbit[8]uril, or cucurbit[10]uril.

5. The method of claim 1, wherein at least part of the guest for cucurbituril exists as a complex with cucurbituril.

6. The method of claim 1, wherein the gold nanoparticle is positively charged.

7. The method of claim 1, wherein the cucurbituril reduces electrostatic attraction between the guest for cucurbituril and the gold salt.

8. The method of claim 1, wherein the gold nanoparticle has a uniform size.

9. The method of claim 1, wherein the molar ratio of the gold salt to the guest for cucurbituril is 1:1 to 2.5:1.

10. The method of claim 1, wherein the reducing step is performed by a reducing agent of $NaBH_4$.

\* \* \* \* \*